United States Patent

Martin et al.

[11] 4,295,827
[45] Oct. 20, 1981

[54] ENDODONTIC FLOW THROUGH ULTRASONIC INSTRUMENT HOLDER ATTACHMENT

[76] Inventors: Howard Martin, 909 Pershing Dr., Silver Spring, Md. 20907; James P. Norris, 1207 Frederick Rd., Catonsville, Md. 21228

[21] Appl. No.: 108,969

[22] Filed: Dec. 31, 1979

[51] Int. Cl.³ .............................................. A61C 5/02
[52] U.S. Cl. ...................................... 433/81; 433/119
[58] Field of Search ................... 433/102, 81, 86, 119, 433/118

[56] References Cited

U.S. PATENT DOCUMENTS 907,003 12/1908 Burnley ............................... 433/161
3,589,012 6/1971 Richman ............................. 433/86

Primary Examiner—Robert Peshock

[57] ABSTRACT

The invention is an improved endodontic apparatus attachment for holding instruments, particularly endodontic drill files that are energized and vibrated by ultrasonic means. The invention also provides for the flow-through of solutions during debriding and irrigating of root canals. The invention consists of a hollow tube-like means for conducting solution and directing it in the axial direction of the endodontic drill file. The hollow tube-like means incorporates a special holding means therein for mounting the drill file in such a position so that ultrasonic waves can be transmitted to the drill file to cause it to vibrate in a manner that improves debriding of the root canal.

12 Claims, 3 Drawing Figures

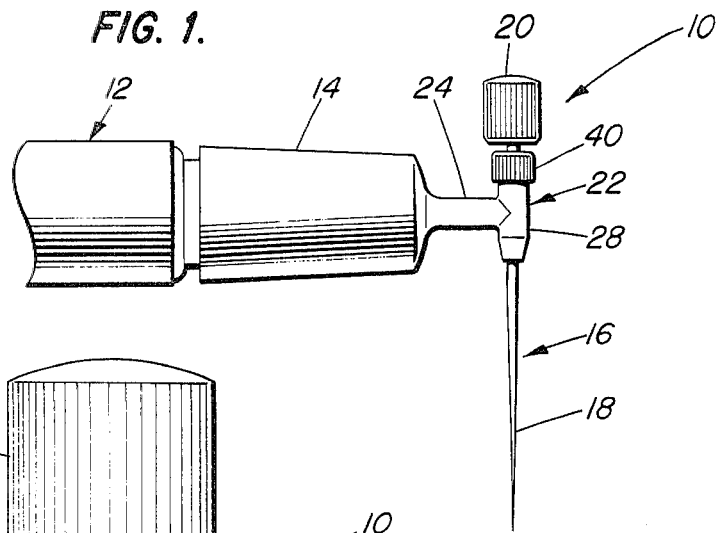
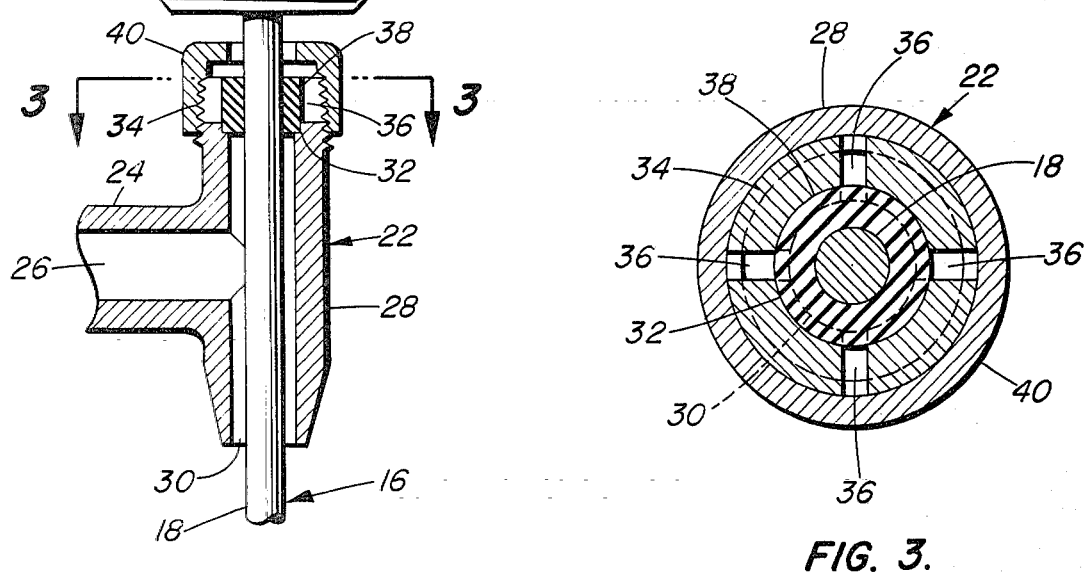
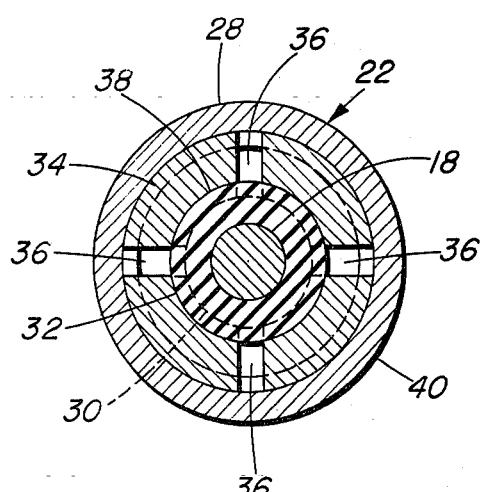

ENDODONTIC FLOW THROUGH ULTRASONIC INSTRUMENT HOLDER ATTACHMENT

BACKGROUND AND SUMMARY OF THE INVENTION

The invention relates to dental instruments and systems and in particular to endodontic instruments and systems. Specifically, the invention relates to an ultrasonic system and an endodontic drill file for debriding root canals. A flow-through means is included for directing a solution along the longitudinal axis of the instrument to irrigate the root canal which is being debrided by the endodontic drill file.

The endodontic flow-through ultrasonic instrument holder attachment of this invention may also be referred to as an endodontic endosonic drill-file holder.

In the prior art the endodontic drill files were primarily operated manually, simultaneously in a more or less vertical-like movement in the more or less longitudinal direction of the root canal and with a partial back and forth rotating motion. Mechanical methods were inadequate. Ultrasonic trials in the prior art were accomplished by rigid connection to the ultrasonic transducer mechanism and were not successful.

Also, in the prior art, irrigation of root canals during treatment was by a separate means which required the drilling action for debriding to cease while the irrigation was performed.

Other irrigating means directed the solution from an external point. This caused considerable "splash-back" and was not satisfactory.

In the present invention these problems of the prior art are overcome. The endodontic drill-file is mounted at one end of the file by a point contact means, instead of a rigid connection at the central axis of the ultrasonic transducer. The end mounting causes the endodontic drill file to vibrate in a series of criss-crossing motions and at the same time the free end tends to vibrate in a movement that is circular-like and/or ellipsoidal or oval.

Coupled with the unique and novel means of mounting the endodontic drill file in the holder, is a hollow tube-like means that transports solution for irrigating the root canal and directing it along the longitudinal axis of the drill file and directly into the root canal. The irrigation, to disinfect, cavitate, shear and acoustic streaming and to flush out debris from the root canal debriding operations of the drill file, can be controlled and used at will without withdrawing the drill file from the root canal.

It is, therefore, an object of the invention to provide a holder attachment for endodontic instruments.

It is another object of the invention to provide a holder attachment specifically for endodontic drill files.

It is also an object of the invention to provide a holder attachment for endodontic instruments which is energized and operated by ultrasonic means.

It is still another object of the invention to provide a holder attachment for endodontic instruments that has flow-through means for directing a solution axially along the instrument.

It is yet another object of the invention to provide a holder attachment for endodontic instruments that mounts the endodontic instruments by point contact to produce a novel vibrating pattern.

Further objects and advantages of the invention will become more apparent in the light of the following description of the preferred embodiments.

BRIEF DESCRIPTION OF THE DRAWINGS

FIG. 1 is a side view of an endodontic instrument holder attached to the end of an ultrasonic mechanism, showing an endodontic instrument mounted therein;

FIG. 2 is a partial side view in section of an endodontic instrument holder, showing a partial view of an endodontic instrument therein; and FIG. 3 is a cross sectional view on line 3—3 of FIG. 2.

DESCRIPTION OF THE PREFERRED EMBODIMENTS

Referring to the drawings, and particularly to FIG. 1, an endodontic flow-through ultrasonic instrument holder attachment is shown at 10.

The instrument holder attachment 10 consists primarily of a horizontal hollow tube-like member 24, a vertical hollow-tube-like member 22, and a knob-like instrument locking means 40, the instrument locking means 40 being associated with other members as hereinafter described.

The instrument holder attachment 10 has a connecting means 14 for connecting or coupling the instrument holder attachment 10 to an ultrasonic transducer mechanism 12. It is to be noted that in FIG. 1 the horizontal hollow tube-like member 24 is shown integral with the connecting means 14. It is to be understood that the horizontal hollow tube-like member 24 and the connecting means 14 may be separate pieces of the structure and suitably affixed to each other, such a variation in the structure is within the scope and intent of this invention.

It is further to be understood that the instrument holder attachment 10 will fit any ultrasonic transducer mechanism 12 merely by the suitable sizing of the connecting means 14 which is then affixed to the horizontal hollow tube-like member 24.

It is to be noted in FIG. 1 that the vertical hollow tube-like member 22 is shown more or less at a right angle to the horizontal hollow tube-like member 24. However, it is to be understood that any inclination of the two hollow tube-like members 22 and 24 to each other at other than a right angle, for purposes of use in endodontic or other dental practices, is within the scope and intent of this invention.

FIG. 1 also shows an endodontic instrument 16 mounted in the instrument holder attachment 10. In this instance an endodontic drill file 18 with end head 20 thereon is the endodontic instrument 16 mounted in the instrument holder attachment 10.

It is to be understood that while the description for this invention relates to an endodontic drill file 16, the instrument holder attachment 10 may be used for, or suitably adapted to, other endodontic or other dental instruments.

Turning now to FIGS. 2 and 3, the instrument holder attachment 10 may be seen in partial section in FIG. 2. The relation of the horizontal hollow tube-like member 24 to the vertical hollow tube-like member 22 and communicating with each other can be seen clearly. The two hollow tube-like members 22 and 24 are shown integral with each other, however, it is to be understood that these two members may be separate elements and suitably affixed to each other, such a variation is within the scope and intent of this invention.

In order to hold the instrument 16 in the instrument holder attachment 10, in this case the endodontic drill file 18 with the end head 20 thereon, the instrument locking means 40 cooperates with the upper or superior end of the vertical hollow tube-like member 22 and a chuck member 38 as hereinafter described.

The vertical hollow tube-like member 22 consists of an open lower end 28 and an externally threaded upper end 34. The passageway 30 extends through the open lower end 28 and the threaded upper end 34 as one continuous passageway. Passageway 30 through the hollow tube-like member 22 communicates with the passageway 26 through the horizontal tube-like member 24.

The externally threaded upper end 34 is counterbored 32 to receive the chuck member 38 therein. A plurality of slots 36 are cut transversely into the externally threaded upper end 34. Four such slots 36 are shown in FIG. 3.

The instrument locking means 40 is internally threaded to mate with the external threads on the threaded end 34. The threads are tapered so that the threaded end 34 will be squeezed inwardly when the instrument locking means 40 is tightened around the segments of the threaded end 34 formed by the slots 36.

The instrument 16, in this case the endodontic drill file 18, with the end head 20 is inserted through a clearance hole (not numbered) in the instrument locking means 40 and then through a close-fitting hole in the chuck member 38. The chuck member 38 is a compressible substance, such as a rubber-like material or neoprene, or other suitable material. The instrument 16 then extends downward through the passageway 30 and extends from the open lower end 28 of the vertical hollow tube-like member 22.

When the instrument locking means 40 is tightened on the threaded end 34, the inward squeezing as hereinbefore described, compresses the chuck member 38 and locks the instrument 16 securely in place. This locking action also seals the upper end of the passageway 30 at the counterbore 32.

Thus, the instrument 16, in this case the endodontic drill file 18 is held securely by a point contact near the end head 20, the balance of the drill file 18 being free and extending out of the instrument holder attachment 10 as illustrated.

When ultrasonic vibrations are produced by the transducer mechanism 12, the vibrations are transmitted through the structure hereinbefore described to the instrument 16, in this case the drill file 18 and cause it to vibrate. The vibrations of the unrestrained end of the instrument 16 occur in all directions due to being a very thin freely extending clamped-free type cantilever member, subsequently the vibrating action takes on a more or less circular-like movement of vibration. This energized circular-like vibrating movement debrides the root canal walls as the instrument is moved in and out of the root canal passageway.

As needed, and at the proper moment, the dentist can irrigate and disinfect the root canal by releasing, through controls, a solution from a source through the passageway 26 which then passes out through passageway 30 axially along the instrument 16 and into the root canal. This same procedure can also be used when other endodontic or dental instruments are used. The irrigation cleans out and cavitates the debris from the debriding action which in endodontic procedure removes tooth structure from the wall of the root canal.

The upper end of the vertical hollow tube-like means 22, being sealed off as described hereinbefore by the chuck member 38 in the counterbore 32, splashback is prevented.

Thus, the instrument holder attachment 10 facilitates both instrumentation and irrigation of root canals or other endodontic or dental work to which it may be adaptable. The instrument holder attachment 10 becomes a velocity transformer for the ultrasonic waves. It is to be noted that ultrasonic waves may also be transmitted down passageway 26 to impinge upon the instrument 16 in passageway 30. In a like manner, when a solution is being passed through the passageway 26, the ultrasonic waves may also be transmitted through the solution as well as the instrument holder attachment 10 structure.

The instrument holder attachment 10 may be made of any suitable material, particularly metal, such as stainless steel or the equivalent that will be compatible and in resonance with an ultrasonic unit for proper impedance.

It is to be noted that in endodontic apparatus the instrument holder attachment 10 may be configured in dimensions of several millimeters, however, it is to be understood that for other instrumentation a configuration of other dimension is within the scope and intent of this invention.

The chuck member 38 and the instrument locking means 40 permit length control of the protruding instrument 16.

The effectiveness of the imposed ultrasonic forces in improving the cutting effectiveness is a function of the ratio of the maximum vibrating tip velocity of the drill file 18 to the peripheral velocity of the drill file 18 relative to the work surface of the root canal.

As can be readily understood from the foregoing description of the invention, the present structure can be configured in different modes to provide the ability to hold an instrument for ultrasonic vibration with a means for flow-through of a solution, for endodontic or other dental work.

Accordingly, modifications and variations to which the invention is susceptible may be practiced without departing from the scope and intent of the appended claims.

What is claimed is:

1. In combination, an endodontic instrument, an ultrasonic transducer device, a holder attachment for said instrument and ultrasonic transducer device, and an instrument locking means, said holder attachment consisting of a first hollow tube-like member and a second hollow tube-like member, said first and second hollow tube-like members being permissively and selectively capable of being set at any one of a plurality of angular relationships to each other, said ultrasonic transducer being coupled to one end of said first hollow tube-like member and with the opposite end of said first hollow tube-like member being coupled and affixed to said second hollow tube-like member at one selected position of said plurality of angular relationships, the interior of said first hollow tube-like member communicating with the interior of said second hollow-tube-like member, said instrument locking means being coupled to one end of said second hollow tube-like member, said endodontic instrument being mounted in said instrument locking means, the opposite end of said second hollow tube-like member being open for passing said endodontic instrument therethrough, said opposite end of said second hollow tube-like member also being open for passing a solution therethrough as and when received from said first hollow tube-like member.

2. The combination of structure as receited in claim 1, wherein said first hollow tube-like member and said second hollow tube-like member each have passageways longitudinally therethrough, said first hollow tube-like member being oriented at a right angle to said second hollow tube-like member for said selected position of said plurality of angular relationships, said orientation at a right angle being at the point where said members are coupled and affixed to each other, said passageways communicating with each other at point of connection, said point of coupling and affixing members being spaced from the ends of said second hollow tube-like member.

3. In combination, a structure, comprising:
an endodontic instrument;
an ultrasonic transducer device;
a holder attachment, said holder attachment being for said instrument and said ultrasonic transducer device, said holder attachment consisting of a first hollow tube-like member, and a second hollow tube-like member, said ultrasonic transducer device being coupled to one end of said first hollow tube-like member and with the opposite end of said first hollow tube-like member being coupled and affixed to said second hollow tube-like member, the interior of said first hollow tube-like member communicating with the interior of said second hollow tube-like member; and
an instrument locking means, said instrument locking means being coupled to one end of said second hollow tube-like member, said endodontic instrument being mounted in said instrument locking means, the opposite end of said second hollow tube-like member being open for passing said endodontic instrument therethrough, said opposite end of said second hollow tube-like member also being open for passing a solution therethrough as and when received from said first hollow tube-like member, said instrument locking means consisting of a plurality of transverse slots in said one end of said second hollow tube-like member, external thread means on said one end of said second hollow tube-like member for mounting said instrument locking means, a counterbore in said one end of said second hollow tube-like member, a clutch member, said clutch member being located in said counterbore, and a knob-like locking member, said knob-like locking member being internally threaded to mate with said external thread on said one end of said second hollow tube-like member.

4. The combination of structure as recited in claim 3, wherein said external thread and said internal thread are tapered threads.

5. The combination of structure as recited in claim 3, wherein said clutch member is of a rubber-like compressible material.

6. The combination of structure as recited in claim 3, wherein said knob-like locking member has a clearance hole centrally located in the end thereof, said clearance hole communicating the interior of said knob-like locking member with the exterior thereof.

7. The combination of structure as recited in claim 5, wherein said clutch member has a passageway therethrough.

8. The combination of structure as recited in claim 3, wherein said first and second hollow tube-like members are stainless steel.

9. The combination of structure as recited in claim 3, wherein said passageways are suitable for conducting a solution from a source for discharge from the open opposite end of said second hollow tube-like member.

10. The combination of structure as recited in claim 9, wherein said endodontic instrument is an endodontic drill file.

11. The combination of structure as recited in claim 3, wherein said first and second hollow tube-like members each have passageways longitudinally therethrough, said first and second hollow tube-like members being permissibly and selectively capable of being set at any one of a plurality of angular relationships to each other, said opposite end of said first hollow tube-like member being coupled and affixed to said second hollow tube-like member at one selected position of said plurality of angular relationships, the point of affixing said first hollow tube-like member to said second hollow tube-like member being spaced from both ends of said second hollow tube-like member.

12. The combination of structure as recited in claim 11, wherein said first hollow tube-like member is oriented at a right angle to said second hollow tube-like member for said selected position of said plurality of angular relationships, said orientation at a right angle being at the point where said members are coupled and affixed to each other.

* * * * *